(12) United States Patent
Sundermann et al.

(10) Patent No.: US 6,943,181 B2
(45) Date of Patent: *Sep. 13, 2005

(54) USE OF SUBSTITUTED GAMMA-LACTONE COMPOUNDS AS PHARMACEUTICAL PREPARATIONS

(75) Inventors: Corinna Sundermann, Aachen (DE); Bernd Sundermann, Aachen (DE); Michael Przewosny, Aachen (DE); Hagen-Heinrich Hennies, Simmerath (DE)

(73) Assignee: Grunenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/751,737

(22) Filed: Jan. 5, 2004

(65) Prior Publication Data

US 2004/0176394 A1 Sep. 9, 2004

Related U.S. Application Data

(63) Continuation of application No. PCT/EP02/07382, filed on Jul. 3, 2002.

(30) Foreign Application Priority Data

Jul. 5, 2001 (DE) .......................................... 101 32 726

(51) Int. Cl.$^7$ ................ A61K 31/4525; A61K 31/4709; A61K 31/4164; A61K 31/506
(52) U.S. Cl. .................. 514/336; 514/255.05; 514/275; 514/313; 514/338; 514/407
(58) Field of Search ........................... 514/255.05, 275, 514/313, 336, 407, 338

(56) References Cited

FOREIGN PATENT DOCUMENTS

| DE | 100 50 663 A 1 | 4/2002 |
|---|---|---|
| WO | WO 91/02725 | 3/1991 |
| WO | WO 01/27109 A2 | 4/2001 |

OTHER PUBLICATIONS

Chabrier, P.E., et al., "Nitric Oxide Synthases: Targets For Therapeutic Strategies In Neurological Diseases", CMLS Cellular and Molecular Life Sciences, 55, (1999), pp. 1029–1035.
Lassen et al., "Nitric Oxide Synthase Inhibition in Migraine", Feb. 8, 1997, Gloucester Gastroenterology Group, Gloucester, UK, pp. 401–402.
Green et al., "Nitric Oxide: From Basic Research to Clinical Applications", Feb. 2, 1999, DDT, vol. 4, pp. 47–49.
Thomsen et al., "Nitric Oxide Theory of Migraine", 1998, Clinical Neuroscience, pp. 28–33.
Hobbs et al., "Inhibition of Nitric Oxide Synthase as a Potential Therapeutic Target", Annu. Rev. Pharmacol. Toxicol., 1999, pp. 191–220.
Murad, Die Entdeckung Einiger Biologischer Wirkungen Von Stickstoffmonoxid Und Seiner Rolle Fur Die Zellkommunikation (Nobel–Vortrag), Angew. Chem., 1999, pp. 1977–1989.
Ignaro, "Stickstoffmonoxid: Ein Einzigartiges Endogenes Signalmolekül In Der Gefaβbiologie (Nobel–Vortag)" Angew. Chem., 1999, pp. 2003–2013.
"Discovery of Some of the Biological Effects of Nitric Oxide and Its Role in Cell Signaling (Nobel Lecture)", Ferid Murad, Angew. Chem. Int. Ed. 1999, 38, pp. 1857–1868.
"Nitric Oxide Synthase Inhibition In Migraine", Lassen et al., The Lancet, 1988, vol. 349, pp. 401–402.

*Primary Examiner*—Bernard Dentz
(74) *Attorney, Agent, or Firm*—Perman & Green, LLP.

(57) ABSTRACT

The invention relates to the use of substituted gamma-lactone compounds in the production of medicines for treating migraines, septic shock, neurodegenerative diseases, such as multiple sclerosis, Parkinsons, Alzheimers or Huntingtons disease, inflammations and related pain, cerebral ischaemia, diabetes, meningitis, arteriosclerosis, cancer, mycosis, or for healing wounds.

20 Claims, 2 Drawing Sheets

USE OF SUBSTITUTED GAMMA-LACTONE COMPOUNDS AS PHARMACEUTICAL PREPARATIONS

Figure 1:
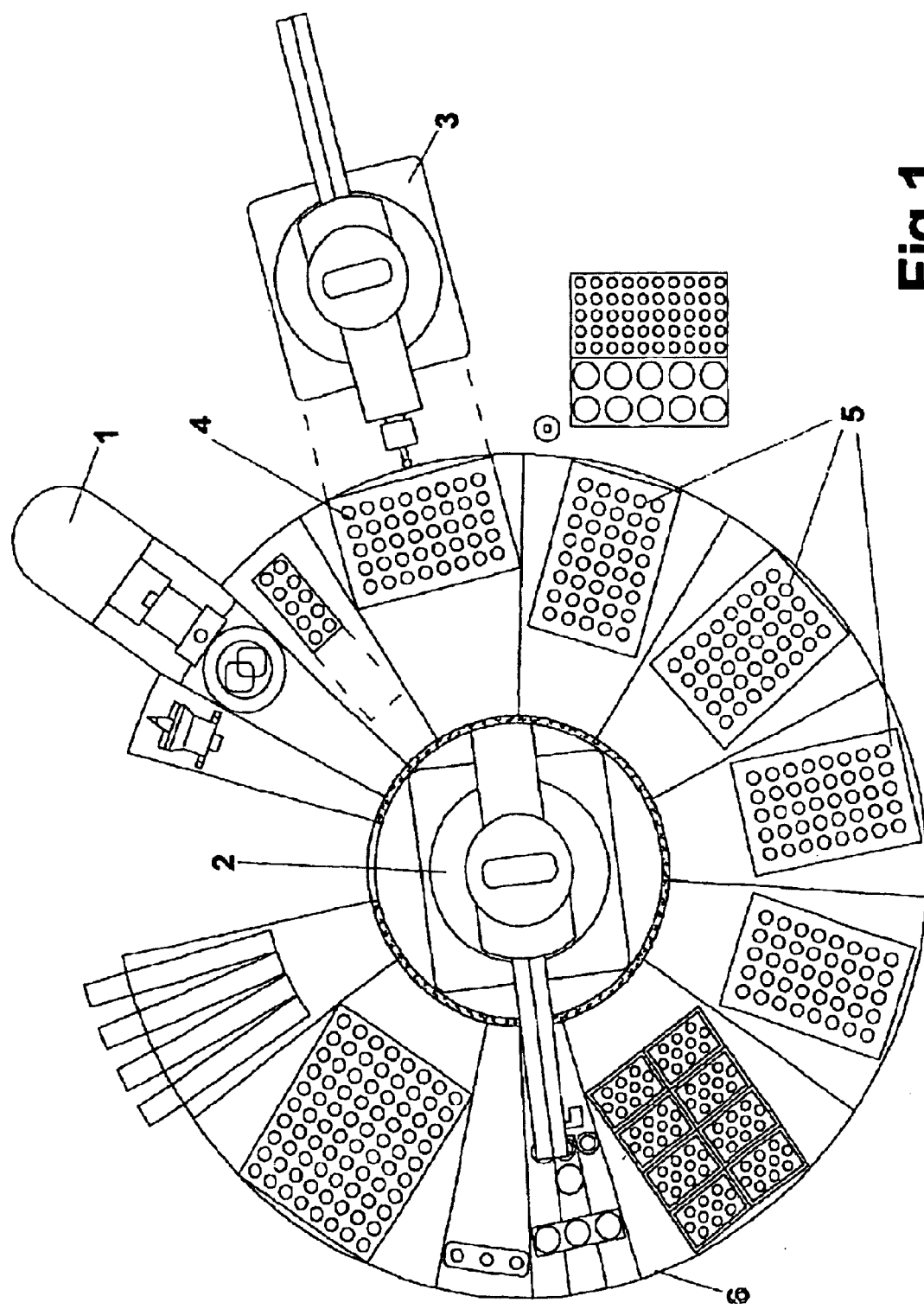

This application is a continuation of international application number PCT/EP02/07382 filed Jul. 3, 2002, status pending.

The present invention relates to the use of substituted γ-lactone compounds for the production of pharmaceutical preparations for the treatment of migraine, septic shock, neurodegenerative diseases, such as multiple sclerosis, Parkinson's disease, Alzheimer's disease or Huntington's chorea, inflammation, inflammatory pain, cerebral ischaemia, diabetes, meningitis, arteriosclerosis, neoplastic diseases, fungal diseases or for wound healing.

Nitrogen monoxide (NO) regulates numerous physiological processes, inter alia neurotransmission, the relaxation and proliferation of smooth muscle, the adhesion and aggregation of thrombocytes as well as tissue injury and inflammation. Due to the large number of signal functions, nitrogen monoxide has been associated with a series of diseases, for example in L. J. Ignarro, Angew. Chem. (1999), 111, pages 2002–2013 and in F. Murad, Angew. Chem. Int. Ed. (1999), 111, pages 1976–1989. Nitrogen monoxide synthase (NO synthase), the enzyme responsible for the physiological formation of nitrogen monoxide, plays an important role in influencing these diseases therapeutically. To date, three different isoforms of NO synthase have been identified, namely the two constitutive forms nNO synthase and eNO synthase together with the inducible form iNO synthase (A. J. Hobbs, A. Higgs, S. Moncada, Annu. Rev. Pharmacol. Toxicol. (1999), 39, pages 191–220; I. C. Green, P.-E. Chabrier, DDT (1999), 4, pages 47–49; P.-E. Chabrieret al., Gell. Mol. Life Sci. (1999), 55, pages 1029–1035).

The inhibition of NO synthase opens up new therapeutic approaches for various diseases which are associated with nitrogen monoxide (A. J. Hobbs et al., Annu. Rev. Pharmacol. Toxicol. (1999), 39, pages 191–220; I. C. Green, P.-E. Chabrier, DDT (1999), 4, pages 47–49; P.-E. Chabrier et al." Gell. Mol. Life Sci. (1999), 55, pages 1029–1035), such as for example migraine (L. L. Thomsen, J. Olesen, Clinical Neuroscience (1998), 5, pages 28–33; L. H. Lassen et al., The Lancet (1997), 349, 401–402), septic shock, neurodegenerative diseases such as multiple sclerosis, Parkinson's disease, Alzheimer's disease or Huntington's chorea, inflammation, inflammatory pain, cerebral ischaemia, diabetes, meningitis and arteriosclerosis.

Inhibition of NO synthase may furthermore have an effect on wound healing, on tumours and on angiogenesis and bring about non-specific immunity towards microorganisms (A. J. Hobbs et al., Annu. Rev. Pharmacol. Toxicol. (1999), 39, pages 191–220).

Hitherto known active ingredients which inhibit NO synthase, apart from L-NMMA and L-NAME (i.e. L-arginine analogues from which nitrogen monoxide and citrulline are formed in vivo with the participation of NO synthase), are inter alia S-methyl-L-citrulline, aminoguanidine, S-methylisourea, 7-nitroindazole and 2-mercaptoethylguanidine (A. J. Hobbs et al., Annu. Rev. Pharmacol. Toxicol. (1999), 39, pages 191–220).

A requirement still remains for further such active ingredients.

One object of the present invention was accordingly to provide active ingredients which act as an inhibitor on nitrogen monoxide synthase. In particular, the pharmaceutical preparations containing such active ingredients are intended to be suitable for the treatment of migraine, septic shock, neurodegenerative diseases, such as multiple sclerosis, Parkinson's disease, Alzheimer's disease or Huntington's chorea, inflammation, inflammatory pain, cerebral ischaemia, diabetes, meningitis, arteriosclerosis, neoplastic diseases, fungal diseases or for wound healing.

It has surprisingly now been found that substituted γ-lactone compounds of the general formula I below act as inhibitors on nitrogen monoxide synthase and are in particular suitable for the production of a pharmaceutical preparation for the treatment of migraine, septic shock, neurodegenerative diseases, such as multiple sclerosis, Parkinson's disease, Alzheimer's disease or Huntington's chorea, inflammation, inflammatory pain, cerebral ischaemia, diabetes, meningitis, arteriosclerosis, neoplastic diseases, fungal diseases or for wound healing.

The present invention accordingly provides the use of at least one substituted γ-lactone compound of the general formula I

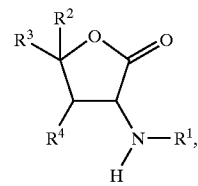

in which $R^1$ denotes an optionally at least mono-substituted 2-pyridyl, 2-pyrimidyl, 2-pyrazolyl, 2-quinolinyl or 2-pyrazinyl residue, which may also be fused with a saturated or at least partially unsaturated hydrocarbon ring system, preferably denotes an optionally at least mono-substituted 2-pyridyl residue, which may also be fused with a saturated or at least partially unsaturated hydrocarbon ring system, particularly preferably denotes a 2-pyridyl residue which is substituted at least in position 4, $R^2$ denotes an optionally at least mono-substituted, saturated, branched or unbranched aliphatic $C_{1-10}$ residue or an optionally at least mono-substituted, at least partially unsaturated, branched or unbranched aliphatic $C_{2-10}$ residue, preferably an optionally at least mono-substituted, branched or unbranched $C_{1-6}$ alkyl residue, $R^3$ denotes an optionally at least mono-substituted aryl residue, $R^4$ denotes H, or $R^3$ and $R^4$ together denote an optionally at least mono-substituted, saturated or at least mono-unsaturated aliphatic $C_{3-7}$ residue, with the proviso that the residue $R^2$ in this case denotes an optionally at least mono-substituted aryl residue, an optionally at least mono-substituted, saturated, branched or unbranched aliphatic $C_{1-10}$ residue or an optionally at least mono-substituted, at least partially unsaturated, branched or unbranched aliphatic $C_{2-10}$ residue, in the form of the racemates, diastereomers or enantiomers thereof as a free base or of a corresponding physiologically acceptable salt for the production of a pharmaceutical preparation for the treatment of migraine, septic shock, neurodegenerative diseases, preferably multiple sclerosis, Parkinson's disease, Alzheimer's disease or Huntington's chorea, inflammation, inflammatory pain, cerebral ischaemia, diabetes, meningitis, arteriosclerosis, neoplastic diseases, fungal diseases or for wound healing.

It is preferred to use at least one substituted γ-lactone compound of the above-stated general formula I, in which R³ denotes an optionally at least mono-substituted aryl residue and R⁴ denotes H and the other residues R¹ and R² have the meaning according to the above-stated general formula I.

The aliphatic residues may be mono- or polysubstituted. If the aliphatic residues comprise more than one substituent, these may be identical or different and be attached both to the same and to different atoms of the aliphatic residue. The aliphatic residue is preferably selected from the group consisting of optionally at least mono-substituted methyl, ethyl, propyl, isopropyl, n-butyl, sec.-butyl, tert-butyl, n-pentyl, neopentyl, n-hexyl, n-heptyl, n-octyl, n-nonyl, n-decyl, propenyl, butenyl, pentenyl, hexenyl, heptenyl, octenyl, propynyl, butynyl, pentynyl, hexynyl, heptynyl and octynyl. The substituents are preferably selected from the group consisting of F, Cl, Br, I, $NH_2$, SH and OH.

For the purposes of the present invention an aryl residue is also taken to mean those aromatic hydrocarbon residues which are fused with a saturated or at least partially unsaturated hydrocarbon ring system.

A preferred aryl residue is an optionally at least mono-substituted phenyl, naphthyl or anthracenyl residue, particularly preferably an optionally mono-substituted phenyl residue. If the aryl residue comprises more than one substituent, these may be identical or different. The substituents are preferably selected from the group consisting of F, Cl, Br, I, $NH_2$, SH, OH, $CF_3$, CN, $NO_2$, $OR^5$, $SR^5$, $NR^6R^7$ and $C_{1-6}$ alkyl, $C_{1-6}$ alkoxy, $C_{2-8}$ alkenyl, $C_{2-8}$ alkynyl, phenyl, phenoxy and benzyloxy which are unsubstituted or at least monosubstituted with F, Cl, Br, I, $NH_2$, SH, OH, $CF_3$, CN or $NO_2$, wherein $R^5$ denotes H, a $C_{1-10}$ alkyl residue, an unsubstituted aryl or heteroaryl residue or denotes an unsubstituted aryl or heteroaryl residue attached via a $C_{1-3}$ alkylene group and $R^6$ and $R^7$, identical or different, denote H, a $C_{1-10}$ alkyl residue, an unsubstituted aryl or heteroaryl residue or denote an unsubstituted aryl or heteroaryl residue attached via a $C_{1-3}$ alkylene group.

If the residue $R^1$ denotes a mono- or polysubstituted 2-pyridyl, 2-pyrimidyl, 2-pyrazolyl, 2-quinolinyl or 2-pyrazinyl residue which is optionally fused with a saturated or at least partially unsaturated hydrocarbon ring system, the substituents may be identical or different and are preferably selected from the group consisting of F, Cl, Br, I, $NH_2$, SH, OH, $CF_3$, CN, $NO_2$, $OR^5$, $SR^5$, $NR^6R^7$ and $C_{1-6}$ alkyl, $C_{1-6}$ alkoxy, $C_{2-8}$ alkenyl, $C_{2-8}$ alkynyl, phenyl, phenoxy and benzyloxy which are unsubstituted or at least monosubstituted with F, Cl, Br, I, $NH_2$, SH, OH, $CF_3$, CN or $NO_2$, wherein the residues $R^5$, $R^6$ and $R^7$ have the above-stated meaning.

For the purposes of the present invention, a heteroaryl residue is understood to mean also those heteroaromatic, hydrocarbon residues which are fused with a saturated or at least partially unsaturated hydrocarbon ring system. The heteroaryl residue preferably contains a heteroatom selected from the group consisting of sulfur, nitrogen and oxygen. The heteroaryl residue is preferably an unsubstituted thiophenyl, furanyl, pyrrolyl, pyridinyl, pyrimidinyl, quinolinyl, isoquinolinyl, phthalazinyl or quinazolinyl residue.

It is particularly preferred to use at least one of the following compounds of the general formula I:

5-(2,4-Dimethyl-phenyl)-3-(8-hydroxy-quinolin-2-ylamino)-5-methyl-dihydro-furan-2-one,
5-(3,4-Dimethyl-phenyl)-3-(4,6-dimethyl-pyridin-2-ylamino)-5-methyl-dihydro-furan-2-one,
5-(2,4-Dimethyl-phenyl)-3-(4,6-dimethyl-pyridin-2-ylamino)-5-methyl-dihydro-furan-2-one,
5-(4-Cyclohexyl-phenyl)-3-(4,6-dimethyl-pyridin-2-ylamino)-5-methyl-dihydro-furan-2-one,
5-(3,5-Dimethyl-phenyl)-3-(4,6-dimethyl-pyridin-2-ylamino)-5-methyl-dihydro-furan-2-one,
5-(3,4-Dimethyl-phenyl)-5-methyl-3-(4-methyl-pyridin-2-ylamino)-dihydro-furan-2-one,
5-(2,4-Dimethyl-phenyl)-5-methyl-3-(4-methyl-pyridin-2-ylamino)-dihydro-furan-2-one,
5-(4-Cyclohexyl-phenyl)-5-methyl-3-(4-methyl-pyridin-2-ylamino)-dihydro-furan-2-one,
5-Methyl-3-(quinolin-2-ylamino)-5-m-tolyl-dihydro-furan-2-one,
3-(4,6-Dimethyl-pyridin-2-ylamino)-5-methyl-5-p-tolyl-dihydro-furan-2-one,
3-(4,6-Dimethyl-pyridin-2-ylamino)-5-methyl-5-m-tolyl-dihydro-furan-2-one,
3-(4,6-Dimethyl-pyridin-2-ylamino)-5-(4-ethoxy-phenyl)-5-methyl-dihydro-furan-2-one,
4-[4-(3-Bromo-5-methyl-pyridin-2-ylamino)-2-methyl-5-oxo-tetrahydro-furan-2-yl]-benzonitrile,
3-(3-Bromo-5-methyl-pyridin-2-ylamino)-5-(4-tert-butyl-phenyl)-5-methyl-dihydro-furan-2-one,
5-(4-tert-Butyl-phenyl)-5-methyl-3-(6-propyl-pyridin-2-ylamino)-dihydro-furan-2-one,
5-(4-tert-Butyl-phenyl)-5-methyl-3-(4-methyl-3-nitro-pyridin-2-ylamino)-dihydro-furan-2-one,
3-(5-Bromo-6-methyl-pyridin-2-ylamino)-5-methyl-5-(4-phenoxy-phenyl)-dihydro-furan-2-one,
5-(4-tert-Butyl-phenyl)-5-methyl-3-(3-nitro-pyridin-2-ylamino)-dihydro-furan-2-one,
3-(3-Benzyloxy-pyridin-2-ylamino)-5-methyl-5-(4-phenoxy-phenyl)-dihydro-furan-2-one,
3-(3-Benzyloxy-pyridin-2-ylamino)-5-(4-tert-butyl-phenyl)-5-methyl-dihydro-furan-2-one,
3-(4,6-Dimethyl-pyridin-2-ylamino)-5-methyl-5-(4-phenoxy-phenyl)-dihydro-furan-2-one,
5-(4-tert-Butyl-phenyl)-3-(4,6-dimethyl-pyridin-2-ylamino)-5-methyl-dihydrofuran-2-one
5-Methyl-3-(4-methyl-pyridin-2-ylamino)-5-(4-phenoxy-phenyl)-dihydro-furan-2-one,
5-(4-tert-Butyl-phenyl)-5-methyl-3-(4-methyl-pyridin-2-ylamino)-dihydro-furan-2-one,
4-[4-(5-Bromo-3-nitro-pyridin-2-ylamino)-2-methyl-5-oxo-tetrahydro-furan-2-yl]-benzonitrile,
4-[4-(5-Bromo-pyrimidin-2-ylamino)-2-methyl-5-oxo-tetrahydro-furan-2-yl]-benzonitrile,
5-Benzo[b]thiophen-2-yl-5-methyl-3-(6-propyl-pyridin-2-ylamino)-dihydro-furan-2-one,
3-(4,6-Dimethyl-pyridin-2-ylamino)-5-(4-isopropyl-phenyl)-5-methyl-dihydro-furan-2-one,
5-Benzofuran-2-yl-3-(4,6-dimethyl-pyridin-2-ylamino)-5-methyl-dihydro-furan-2-one,
5-Benzo[b]thiophen-2-yl-5-methyl-3-(4-methyl-pyridin-2-ylamino)-dihydro-furan-2-one,
5-Benzofuran-2-yl-5-methyl-3-(4-methyl-pyridin-2-ylamino)-dihydro-furan-2-one,
3-(5-Benzo[1,3]dioxol-5-yl-5-methyl-2-oxo-tetrahydro-furan-3-ylamino)-1H-pyrazole-4-carbonitrile,
3-(5-Benzo[1,3]dioxol-5-yl-5-methyl-2-oxo-tetrahydro-furan-3-ylamino)-1H-pyrazole-4-carboxylic acid ethyl ester,
5-Benzo[1,3]dioxol-5-yl-5-methyl-3-(3-nitro-pyridin-2-ylamino)-dihydro-furan-2-one,
3-(4,6-Dimethyl-pyridin-2-ylamino)-5-methyl-5-(5,6,7,8-tetrahydro-naphthalen-2-yl)-dihydro-furan-2-one,
3-(4,6-Dimethyl-pyridin-2-ylamino)-S-methyl-5-naphthalen-2-yl-dihydro-furan-2-one, 5-Benzo[1,3]dioxol-5-yl-5-methyl-3-(4-methyl-pyridin-2-ylamino)-dihydro-furan-2-one,
5-Methyl-3-(4-methyl-pyridin-2-ylamino)-5-(5,6,7,8-tetrahydro-naphthalen-2-yl)-dihydro-furan-2-one,
5-Benzo[1,3]dioxol-5-yl-5-methyl-3-(5-methyl-pyridin-2-ylamino)-dihydro-furan-2-one,
5-Benzo[1,3]dioxol-5-yl-5-methyl-3-(6-methyl-pyridin-2-ylamino)-dihydro-furan-2-one,
3-(5-Bromo-3-nitro-pyridin-2-ylamino)-5-methyl-5-(5,6,7,8-tetrahydro-naphthalen-2-yl)-dihydro-furan-2-one,
3-(5-Bromo-3-nitro-pyridin-2-ylamino)-5-isopropyl-5-phenyl-dihydro-furan-2-one,
5-Isopropyl-3-(5-nitro-pyridin-2-ylamino)-5-phenyl-dihydro-furan-2-one,
5-Methyl-5-naphthalen-2-yl-3-(5-nitro-pyridin-2-ylamino)-dihydro-furan-2-one,
5-Isopropyl-5-phenyl-3-(pyrimidin-2-ylamino)-dihydro-furan-2-one,
3-[5-(4-Iodo-phenyl)-5-methyl-2-oxo-tetrahydro-furan-3-ylamino]-1H-pyrazole-4-carboxylic acid ethyl ester,
5-(4-Bromo-phenyl)-3-(5-bromo-pyridin-2-ylamino)-5-methyl-dihydro-furan-2-one,
3-(3-Bromo-5-methyl-pyridin-2-ylamino)-5-methyl-5-naphthalen-1-yl-dihydro-furan-2-one,
5-Methyl-5-naphthalen-1-yl-3-(6-propyl-pyridin-2-ylamino)-dihydro-furan-2-one,
5-(3-Chloro-phenyl)-5-methyl-3-(6-propyl-pyridin-2-ylamino)-dihydro-furan-2-one,
5-(3-Chloro-phenyl)-5-methyl-3-(4-methyl-3-nitro-pyridin-2-ylamino)-dihydro-furan-2-one,
5-(4-Bromo-phenyl)-5-methyl-3-(4-methyl-3-nitro-pyridin-2-ylamino)-dihydro-furan-2-one,
3-(5-Bromo-6-methyl-pyridin-2-ylamino)-5-methyl-5-naphthalen-1-yl-dihydro-furan-2-one,
3-(5-Bromo-6-methyl-pyridin-2-ylamino)-5-(4-iodo-phenyl)-5-methyl-dihydro-furan-2-one,
3-(3-Benzyloxy-pyridin-2-ylamino)-5-(4-iodo-phenyl)-5-methyl-dihydro-furan-2-one,
3-(3-Benzyloxy-pyridin-2-ylamino)-5-(4-bromo-phenyl)-5-methyl-dihydro-furan-2-one,
3-(4,6-Dimethyl-pyridin-2-ylamino)-5-(4-iodo-phenyl)-5-methyl-dihydro-furan-2-one,
5-(3-Chloro-phenyl)-3-(4,6-dimethyl-pyridin-2-ylamino)-5-methyl-dihydro-furan-2-one,
5-(4-Bromo-phenyl)-5-methyl-3-(3-methyl-pyridin-2-ylamino)-dihydro-furan-2-one,
5-(4-Bromo-phenyl)-5-methyl-3-(4-methyl-pyridin-2-ylamino)-dihydro-furan-2-one,
2-[5-(3,5-Dimethoxy-phenyl)-5-methyl-2-oxo-tetrahydro-furan-3-ylamino]-4-propyl-pyrimidine-5-carboxylic acid ethyl ester,
3-(4-Bromo-1H-pyrazol-3-ylamino)-5-(3,5-dimethoxy-phenyl)-5-methyl-dihydro-furan-2-one,
3-(4-Bromo-1H-pyrazol-3-ylamino)-5-(2-methoxy-phenyl)-5-methyl-dihydro-furan-2-one,
3-[5-(2,5-Dimethoxy-phenyl)-5-methyl-2-oxo-tetrahydro-furan-3-ylamino]-1H-pyrazole-4-carbonitrile,
3-[5-(2,5-Dimethoxy-phenyl)-5-methyl-2-oxo-tetrahydro-furan-3-ylamino]-5-methylsulfanyl-1H-pyrazole-4-carbonitrile,
5-(2,5-Dimethoxy-phenyl)-5-methyl-3-(pyridin-2-ylamino)-dihydro-furan-2-one,
5-(2-Methoxy-phenyl)-5-methyl-3-(pyridin-2-ylamino)-dihydro-furan-2-one,
3-(3-Chloro-5-trifluoromethyl-pyridin-2-ylamino)-5-(3,5-dimethoxy-phenyl)-5-methyl-dihydro-furan-2-one,
3-(3-Chloro-5-trifluoromethyl-pyridin-2-ylamino)-5-(2,5-dimethoxy-phenyl)-5-methyl-dihydro-furan-2-one,
3-(3,5-Dichloro-pyridin-2-ylamino)-5-(2-methoxy-phenyl)-5-methyl-dihydro-furan-2-one,
3-(3-Chloro-5-trifluoromethyl-pyridin-2-ylamino)-5-(2,4-dimethoxy-phenyl)-5-methyl-dihydro-furan-2-one,
3-(4,6-Dimethyl-pyridin-2-ylamino)-5-(3-methoxy-phenyl)-5-methyl-dihydro-furan-2-one,
3-(4,6-Dimethyl-pyridin-2-ylamino)-5-(4-methoxy-phenyl)-5-methyl-dihydro-furan-2-one,
5-(3,4-Dimethoxy-phenyl)-3-(4,6-dimethyl-pyridin-2-ylamino)-5-methyl-dihydro-furan-2-one,
5-(4-Methoxy-phenyl)-5-methyl-3-(4-methyl-pyridin-2-ylamino)-dihydro-furan-2-one,
5-(2,5-Dimethoxy-phenyl)-5-methyl-3-(pyrazin-2-ylamino)-dihydro-furan-2-one,
5-Methylsulfanyl-3-(2-oxo-5-phenyl-5-propyl-tetrahydro-furan-3-ylamino)-1H-pyrazole-4-carbonitrile or a corresponding physiologically acceptable salt, preferably the corresponding hydrochloride.

The substituted γ-lactone compounds of the above-stated general formula I used according to the invention may preferably be produced as described below:

The γ-lactone compounds of the general formula I used according to the invention, in which the residues $R^1$ to $R^4$ have the above-stated meaning, are preferably produced by reacting at least one amine component of the general formula II

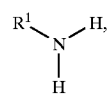

in which the residue $R^1$ has the above-stated meaning, with glyoxalic acid, preferably in form of the monohydrate or an aqueous solution, and at least one alkene component of the general formula III

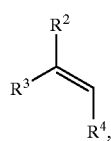

in which the residues $R^2$ to $R^4$ have the above-stated meaning, in the presence of at least one organic and/or inorganic acid, preferably trifluoroacetic acid in an organic solvent to yield at least one compound of the above-stated general formula I and this is optionally purified using conventional methods and/or optionally isolated using conventional methods.

The quantities of the reaction components and of the inorganic and/or organic acid to be used in each case, the temperature during the reaction and the duration of the reaction may vary. The suitable quantity of the components to be used for the particular reaction, the suitable temperature and the suitable duration of the reaction may be determined by the person skilled in the art by simple preliminary testing. The temperature during the reaction is preferably 0 to 100° C., particularly preferably 15 to 40° C. The duration of the reaction is preferably 0.25 to 12 hours.

Acetonitrile or a mixture containing acetonitrile is preferably used as a suitable solvent.

Figure 2:
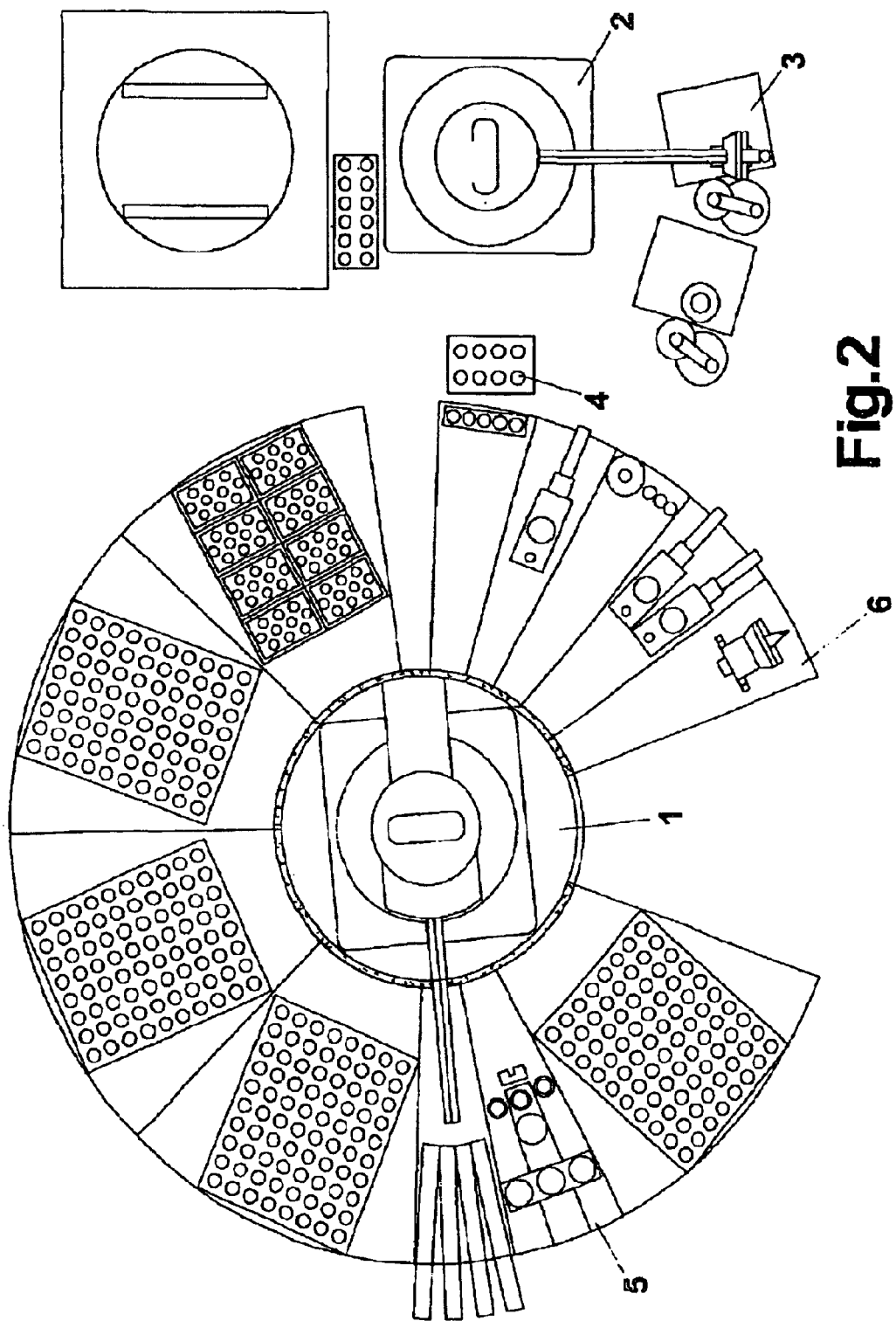

The substituted γ-lactone compounds used according to the invention are preferably produced as described below on an automatic synthesis system from Zymark as shown in FIG. 1 and FIG. 2.

Instead of the above-described reaction of the reaction components of the general formulae II and III and glyoxalic acid, these components may optionally also be reacted in the presence of an inorganic and/or organic acid with microwave irradiation or with exposure to ultrasound.

The γ-lactone compounds of the general formula I used according to the invention, in which the residues $R^1$ to $R^4$ have the above-stated meaning, are accordingly also preferably produced by reacting at least one amine component of the above-stated general formula II, in which $R^1$ has the above-stated meaning, with glyoxalic acid, preferably in form of the monohydrate or an aqueous solution, and at least one alkene component of the above-stated general formula III, in which $R^2$ to $R^4$ have the above-stated meaning, in an organic solvent, optionally in the presence of at least one inorganic and/or organic acid with microwave irradiation or with exposure to ultrasound, preferably with microwave irradiation, to yield at least one compound of the above stated general formula I and this is optionally purified using conventional methods and/or optionally isolated using conventional methods.

The quantities of the reaction components used, the suitable temperature during the reaction and the suitable duration of the reaction may vary. The optimum quantity of the components to be used for the particular reaction, the optimum temperature and the optimum duration of the reaction may be determined by the person skilled in the art by simple preliminary testing. If the reaction proceeds with microwave irradiation, the temperature is 40 to 70° C., particularly preferably 45 to 60° C. The duration of the reaction is preferably 0.1 to 60 minutes for microwave irradiation.

Acetonitrile or a mixture containing acetonitrile is preferably used as a suitable solvent.

The particular reaction components of the general formulae II and III and the glyoxalic acid may be purchased commercially or be produced using conventional methods known to the person skilled in the art.

The substituted γ-lactone compounds of the general formula I used according to the invention may be isolated as the free base or as the salt using the above-described method. The free base of the respective compound according to the invention of the general formula I may preferably be converted into the corresponding physiologically acceptable salt using conventional methods known to the person skilled in the art by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid.

The free base of the respective compound of the general formula I according to the invention may also be converted into the corresponding physiologically acceptable salt with the free acid or a salt of a sugar substitute, such as for example saccharin, cyclamate or acesulfame.

Conversion of the free base of the respective compound of the general formula I into the corresponding hydrochloride may preferably also be obtained by combining the compound of the general formula I, dissolved in a suitable organic solvent, such as for example butan-2-one (methyl ethyl ketone), as a free base with trimethylsilyl chloride (TMSCl).

If the substituted γ-lactone compounds of the general formula I used according to the invention are obtained using the above-described production process in the form of the racemates or other mixtures of the various enantiomers and/or diastereomers thereof, these may, if necessary, be separated and optionally isolated using conventional methods known to the person skilled in the art. Examples are chromatographic separation processes, in particular liquid chromatography processes at standard pressure or at elevated pressure, preferably MPLC and HPLC methods, and fractional crystallisation processes. Individual enantiomers, e.g. diastereomeric salts formed by means of HPLC on a chiral phase or by means of crystallisation with chiral acids, such as (+)-tartaric acid, (−)-tartaric acid or (+)-10-camphorsulfonic acid, may here in particular be separated from one another.

The γ-lactone compounds of the general formula I used according to the invention are toxicologically safe and are therefore suitable as pharmaceutical active ingredients in pharmaceutical preparations.

The corresponding pharmaceutical preparations may also contain mixtures of various stereoisomers of one or more γ-lactone compounds according to the invention. For example, various enantiomers of a γ-lactone compound of the general formula I may also be present in non-equimolar quantities.

In addition to at least one substituted γ-lactone compound, the corresponding pharmaceutical preparations conventionally contain further physiologically acceptable auxiliary substances, which are preferably selected from the group consisting of matrix materials, fillers, solvents, diluents, dyes and binders. The corresponding pharmaceutical preparations may be present as liquid, semisolid or solid dosage forms, for example in the form of solutions for injection, drops, succi, syrups, sprays, suspensions, tablets, patches, capsules, transdermal delivery systems, suppositories, ointments, creams, lotions, gels, emulsions, aerosols or in multiparticulate form, for example in the form of pellets or granules, and also be administered as such.

Selection of the physiologically acceptable auxiliary substances and the quantities thereof which are to be used depends upon whether the respective pharmaceutical preparation is to be administered orally, perorally, parenterally, intravenously, intraperitoneally, intradermally, intramuscularly, intranasally, buccally, rectally or topically, for example onto infections of the skin, mucous membranes or eyes. Preparations in the form of tablets, coated tablets, capsules, granules, drops, succi and syrups are, for example, suitable for oral administration, while solutions, suspensions, easily reconstitutible dried preparations and sprays are suitable for parenteral, topical and inhalatory administration. Substituted γ-lactone compounds of the general formula I in a depot in dissolved form or in a dressing, optionally with the addition of skin penetration promoters, are suitable percutaneous administration preparations. Orally or percutaneously administrable formulations may release the substituted γ-lactone compounds in delayed manner.

Production of the pharmaceutical preparations proceeds with the assistance of conventional means, devices, methods and processes known to the person skilled in the art, such as are described for example in "Remington's Pharmaceutical Sciences", Ed. A. R. Gennaro, 17th ed., Mack Publishing Company, Easton, Pa. (1985), in particular in part 8, chapters 76 to 93. The corresponding literature description is hereby introduced as a reference and is deemed to be part of the disclosure.

The quantity of the respective substituted γ-lactone compound of the general formula I to be administered to the patient may vary and is for example dependent on the weight or age of the patient and on the mode of administration, the indication and the severity of the complaint. Conventionally, 0.02 to 500 mg per kg, preferably 0.2 to 5 mg, of patient body weight of at least one substituted γ-lactone compound of the general formula I are administered.

Molecular Pharmacological Investigations:

The assays used for determining the inhibition of nitrogen monoxide synthase by the compounds of the general formula I used according to the invention are described below:

Nitrogen Monoxide Synthase (NOS) Assay

This assay makes it possible to determine the percentage inhibition of NO synthase by a compound of the general formula I used according to the invention by measuring NOS activity on exposure to the compound. NO synthase is here mixed under suitable conditions together with radioactively labelled arginine and the particular compound of the general formula I. After termination of the NO formation reaction at a predetermined time, the quantity of unconverted arginine is directly or indirectly determined. Comparing this quantity with the quantity of arginine remaining in the mixture of NOS and arginine without addition of a compound of the general formula I and under otherwise identical conditions reveals the percentage inhibition of NO synthase by the compound under test. This assay may be carried out at follows:

(a) Incubation of the NO synthase with labelled arginine as the substrate in a reaction vessel,
(b) Separation of the labelled arginine from the labelled citrulline optionally arising as a product of the enzymatic reaction at a time at which the concentration of citrulline is rising,
(c) Measurement of the quantity of arginine separated in each case.

Separation is performed by means of a filter plate membrane.

This NOS assay is in particular suitable for "High Throughput Screening" (HTS) on microtitre plates (MTP).

HTS-NOS Assay: General Method

Radioactive arginine is used as the substrate in this HTS-NOS assay. Depending on the type of microtitre plate (MTP), the assay volume may be selected in the range between 25 μl and 250 μl. Depending on the enzyme source used, cofactors and coenzymes are added. The batches are incubated in this microtitre plate (assay MTP) according to step (a) at room temperature and, depending on the enzyme activity used (units), lasts between 5 and 60 minutes. On completion of incubation (step (a)), the plate is placed in a cell harvester, which is equipped with an MTP which has a cation exchange membrane as a filter bottom (filter MTP). All the batches from the assay MTP are transferred into this filter MTP and suction filtered through a cation exchange filter plate, a paper filter loaded with phosphate groups. The filter MTP is then washed with buffer or water. This procedure binds the remaining substrate arginine onto the cation exchanger, while the enzymatically formed radioactive citrulline is quantitatively eluted. Once the filter MTP has been dried and scintillation liquid added, the bound arginine can be counted in the scintillation counter. Low radioactivity indicates an uninhibited NOS reaction. An inhibited enzyme reaction means that the radioactive arginine has not been converted. This means that there is a high level of radioactivity on the filter.

Materials Used

Arginine, L-[2,3,4-$^3$H]-monohydrochloride; item no. NET-1123, supplier NEN $CaCl_2$ anhydrous; item no. 2388.1000; supplier Merck KGaA 1,4-Dithiothreitol (DTT), item no. 708984; supplier ROCHE $Na_2$EDTA dihydrate; item no. 03680; supplier FLUKA HEPES, item no. H-3375; supplier SIGMA NADPH, tetrasodium salt; item no. 1585363; supplier ROCHE TRIS; item no. 93349; supplier FLUKA Enzyme preparation buffer: 50 mM tris-HCl with 1 mM EDTA: the pH value of the buffer was adjusted to 7.4 at 4° C.

Incubation buffer 50 mM HEPES with 1 mM EDTA; (medium): 1.25 mM $CaCl_2$ and 1 mM dithiothreitol. The pH value of the buffer was adjusted to 7.4 at 25° C.

Washing medium: $H_2O$

Enzyme Preparation

Rat cerebella were used as the starting tissue. The animals were stunned and killed, the brain tissue, the cerebellum, was dissected out, 1 ml of enzyme preparation buffer (4° C.) was added per cerebellum, and the tissue was disrupted for 1 min at 6000 rpm in a Polytron homogeniser. The mixture was then centrifuged at 4° C. for 15 min at 20,000 g, and the supernatant was then decanted off and frozen in portions at −80° C. (discarding the precipitate).

Incubation Batch:

96-Well MTPs with a well capacity of ≦250 μl were used

Pipetting sequence: see table 1:

TABLE 1

| Substance | Molarity (in batch) | μl | *Protein (in batch) |
|---|---|---|---|
| Incubation buffer | — | 100 | — |
| Test substance | variable; preferably $10^{-5}$ M | variable; preferably 20 μl | — |
| NADPH | 0.5 mM | 20 | — |
| Enzyme | — | variable; maximum volume of enzyme solution = 50 μl | variable; maximum usable quantity of protein = 100 μg |
| [$^3$H] substrate | variable; preferably 50 nM | variable; preferably 10 μl | — |
| Final volume: | | max. 250 μl | |

The protein determination was performed in accordance with O. H. Lowry et al.; J. Biol. Chem. 193, 265 (1951). The corresponding literature description is hereby introduced as a reference and is deemed to be part of the disclosure.

Once the pipetting operation was complete, a lid was laid on top of this MTP (assay MTP). Incubation at 25° C. (room temperature (RT)) for 5–60 min, depending on the quantity and activity of the enzyme used.

The contents of the assay MTP were then transferred with the assistance of a 96 well cell harvester into a 96 well cation exchange MTP (filter MTP) and suction filtered. A single washing with 200 ml of $H_2O$ (from a trough) was then performed.

The plate was then dried for 1 h at 60° C. in a drying cabinet. The bottom of the filter MTP was then carefully sealed from beneath with a "back seal". 35 μl of scintillating material were then pipetted into each well. The top of the plate was also sealed with a "top seal". After 1 hour's waiting time, the plate was assessed on the β-counter.

For the purposes of performing HTS, the incubation medium, NADPH and enzyme solution were combined before the beginning of the pipetting step so that it would not be necessary to carry out three separate time-consuming pipetting operations.

The invention is explained below with reference to Examples. These explanations are given merely by way of example and do not restrict the general concept of the invention.

EXAMPLES

The chemicals and solvents used for the production of γ-lactone compounds of the general formula I were purchased commercially, for example from Acros, Avocado, Aldrich, Fluka, Lancaster, Maybridge, Merck, Sigma or TCI or produced using conventional methods known to the person skilled in the art.

Thin-layer chromatography was performed with precoated silica gel 60 F 254 HPTLC plates from E. Merck, Darmstadt.

The yields of the compounds produced have not been optimised.

Analysis was performed by ESI mass spectroscopy or NMR spectroscopy.

General Procedure 1:

The γ-lactone compounds of the general formula I were synthesised on an automatic synthesis system from Zymark as shown in FIG. 1 and FIG. 2.

FIG. 1 shows a capper station (ref. numeral 1) for closing the reaction microtubes, a robot 1 (ref. numeral 2) and a robot 2 (ref. numeral 3), wherein the robot 1 moves the reaction microtubes or the corresponding racks and robot 2 pipettes the reagents into the reaction microtubes, a temperature-controllable reactor block (ref. numeral 4), stirring blocks (ref. numeral 5) and a filtration station (ref. numeral 6), in which the reaction solution is filtered off.

FIG. 2 likewise shows a robot 1 (ref. numeral 1) and a robot 2 (ref. numeral 2), both of which move the glass microtubes holding the synthesis products to the various stations. In detail, the stations comprise a vortexer (ref. numeral 3) for mixing the samples and for apportioning solutions or solvents, a spin reactor (ref. numeral 4) for mixing samples, a phase detection station (ref. numeral 5) for detecting the phase boundary and phase separation and a station (ref. numeral 6) for drying the synthesis products by means of salt cartridges.

For the purposes of synthesis, a round-bottomed glass microtube (diameter 16 mm, length 125 mm) with thread was provided manually with a stirrer and closed on the capper station (ref. numeral 1) according to FIG. 1 with a screw cap with septum. The tube was placed by robot 1 (ref. numeral 2) in the reactor block (ref. numeral 4), which was temperature-controlled to 20° C. Robot 2 (ref. numeral 3) pipetted in the following reagents in succession:

1.) 1 ml of a solution of trifluoroacetic acid and the particular amine component, in each case 0.1 M in acetonitrile,
2.) 1 ml of a 0.11 M glyoxalic acid monohydrate solution in acetonitrile
3.) 1 ml of a 0.3 M solution of the particular alkene component in acetonitrile The reaction mixture was then stirred at 20° C. in one of the stirring blocks (ref. numeral 5) for 600 minutes. The reaction solution was then filtered off in the filtration station (ref. numeral 6). The tube was here rinsed twice with 1.5 ml portions of a 7.5 wt. % sodium hydrogencarbonate solution.

The rack holding the tubes was then placed manually onto an automatic working up unit according to FIG. 2, where the reaction mixture was combined and shaken with 2 ml of diethyl ether on a vortexer (ref. numeral 3).

Thorough mixing was then performed for ten minutes in the spin reactor (ref. numeral 4) and a distinct phase boundary was formed by slowly decreasing the rotary motion. This phase boundary was detected optically on the phase detection station (ref. numeral 5) and the organic phase was removed by pipette. In the next step, the aqueous phase was again combined with 2 ml of diethyl ether, shaken, centrifuged and the organic phase removed by pipette. The combined organic phases were dried over 2.4 g of $MgSO_4$ (pellets). The solvent was removed in a vacuum centrifuge. Each sample was then analysed by electron spray ionisation mass spectrometry (ESI-MS) and/or NMR spectroscopy.

Automated synthesis ensures identical treatment for all samples and consistent reaction control. The γ-lactone compounds according to the examples and produced in accordance with the above general procedure are listed in Table 2 below:

TABLE 2

| Example | Name of compound: |
|---|---|
| 1 | 5-(2,4-Dimethyl-phenyl)-3-(8-hydroxy-quinolin-2-ylamino)-5-methyl-dihydro-furan-2-one |
| 2 | 5-(3,4-Dimethyl-phenyl)-3-(4,6-dimethyl-pyridin-2-ylamino)-5-methyl-dihydro-furan-2-one |
| 3 | 5-(2,4-Dimethyl-phenyl)-3-(4,6-dimethyl-pyridin-2-ylamino)-5-methyl-dihydro-furan-2-one |
| 4 | 5-(4-Cyclohexyl-phenyl)-3-(4,6-dimethyl-pyridin-2-ylamino)-5-methyl-dihydro-furan-2-one |
| 5 | 5-(3,5-Dimethyl-phenyl)-3-(4,6-dimethyl-pyridin-2-ylamino)-5-methyl-dihydro-furan-2-one |
| 6 | 5-(3,4-Dimethyl-phenyl)-5-methyl-3-(4-methyl-pyridin-2-ylamino)-dihydro-furan-2-one |
| 7 | 5-(2,4-Dimethyl-phenyl)-5-methyl-3-(4-methyl-pyridin-2-ylamino)-dihydro-furan-2-one |
| 8 | 5-(4-Cyclohexyl-phenyl)-5-methyl-3-(4-methyl-pyridin-2-ylamino)-dihydro-furan-2-one |
| 9 | 5-Methyl-3-(quinolin-2-ylamino)-5-m-tolyl-dihydro-furan-2-one |
| 10 | 3-(4,6-Dimethyl-pyridin-2-ylamino)-5-methyl-5-p-tolyl-dihydro-furan-2-one |
| 11 | 3-(4,6-Dimethyl-pyridin-2-ylamino)-5-methyl-5-m-tolyl-dihydro-furan-2-one |
| 12 | 3-(4,6-Dimethyl-pyridin-2-ylamino)-5-(4-ethoxy-phenyl)-5-methyl-dihydro-furan-2-one |
| 13 | 4-[4-(3-Bromo-5-methyl-pyridin-2-ylamino)-2-methyl-5-oxo-tetrahydro-furan-2-yl]-benzonitrile |
| 14 | 3-(3-Bromo-5-methyl-pyridin-2-ylamino)-5-(4-tert-butyl-phenyl)-5-methyl-dihydro-furan-2-one |
| 15 | 5-(4-tert-Butyl-phenyl)-5-methyl-3-(6-propyl-pyridin-2-ylamino)-dihydro-furan-2-one |
| 16 | 5-(4-tert-Butyl-phenyl)-5-methyl-3-(4-methyl-3-nitro-pyridin-2-ylamino)-dihydro-furan-2-one |
| 17 | 3-(5-Bromo-6-methyl-pyridin-2-ylamino)-5-methyl-5-(4-phenoxy-phenyl)-dihydro-furan-2-one |
| 18 | 5-(4-tert-Butyl-phenyl)-5-methyl-3-(3-nitro-pyridin-2-ylamino)-dihydro-furan-2-one |
| 19 | 3-(3-Benzyloxy-pyridin-2-ylamino)-5-methyl-5-(4-phenoxy-phenyl)-dihydro-furan-2-one |
| 20 | 3-(3-Benzyloxy-pyridin-2-ylamino)-5-(4-tert-butyl-phenyl)-5-methyl-dihydro-furan-2-one |
| 21 | 3-(4,6-Dimethyl-pyridin-2-ylamino)-5-methyl-5-(4-phenoxy-phenyl)-dihydro-furan-2-one |
| 22 | 5-(4-tert-Butyl-phenyl)-3-(4,6-dimethyl-pyridin-2-yl-amino)-5-methyl-dihydrofuran-2-one |
| 23 | 5-Methyl-3-(4-methyl-pyridin-2-ylamino)-5-(4-phenoxy-phenyl)-dihydro-furan-2-one |
| 24 | 5-(4-tert-Butyl-phenyl)-5-methyl-3-(4-methyl-pyridin-2-ylamino)-dihydro-furan-2-one |
| 25 | 4-[4-(5-Bromo-3-nitro-pyridin-2-ylamino)-2-methyl-5-oxo-tetrahydro-furan-2-yl]-benzonitrile |
| 26 | 4-[4-(5-Bromo-pyrimidin-2-ylamino)-2-methyl-5-oxo-tetrahydro-furan-2-yl]-benzonitrile |

TABLE 2-continued

| Example | Name of compound: |
|---|---|
| 27 | 5-Benzo[b]thiophen-2-yl-5-methyl-3-(6-propyl-pyridin-2-ylamino)-dihydro-furan-2-one |
| 28 | 3-(4,6-Dimethyl-pyridin-2-ylamino)-5-(4-isopropyl-phenyl)-5-methyl-dihydro-furan-2-one |
| 29 | 5-Benzofuran-2-yl-3-(4,6-dimethyl-pyridin-2-ylamino)-5-methyl-dihydro-furan-2-one |
| 30 | 5-Benzo[b]thiophen-2-yl-5-methyl-3-(4-methyl-pyridin-2-ylamino)-dihydro-furan-2-one |
| 31 | 5-Benzofuran-2-yl-5-methyl-3-(4-methyl-pyridin-2-ylamino)-dihydro-furan-2-one |
| 32 | 3-(5-Benzo[1,3]dioxol-5-yl-5-methyl-2-oxo-tetrahydro-furan-3-ylamino)-1H-pyrazole-4-carbonitrile |
| 33 | 3-(5-Benzo[1,3]dioxol-5-yl-5-methyl-2-oxo-tetrahydro-furan-3-ylamino)-1H-pyrazole-4-carboxylic acid ethyl ester |
| 34 | 5-Benzo[1,3]dioxol-5-yl-5-methyl-3-(3-nitro-pyridin-2-ylamino)-dihydro-furan-2-one |
| 35 | 3-(4,6-Dimethyl-pyridin-2-ylamino)-5-methyl-5-(5,6,7,8-tetrahydro-naphthalen-2-yl)-dihydro-furan-2-one |
| 36 | 3-(4,6-Dimethyl-pyridin-2-ylamino)-5-methyl-5-naphthalen-2-yl-dihydro-furan-2-one |
| 37 | 5-Benzo[1,3]dioxol-5-yl-5-methyl-3-(4-methyl-pyridin-2-ylamino)-dihydro-furan-2-one |
| 38 | 5-Methyl-3-(4-methyl-pyridin-2-ylamino)-5-(5,6,7,8-tetrahydro-naphthalen-2-yl)-dihydro-furan-2-one |
| 39 | 5-Benzo[1,3]dioxol-5-yl-5-methyl-3-(5-methyl-pyridin-2-ylamino)-dihydro-furan-2-one |
| 40 | 5-Benzo[1,3]dioxol-5-yl-5-methyl-3-(6-methyl-pyridin-2-ylamino)-dihydro-furan-2-one |
| 41 | 3-(5-Bromo-3-nitro-pyridin-2-ylamino)-5-methyl-5-(5,6,7,8-tetrahydro-naphthalen-2-yl)-dihydro-furan-2-one |
| 42 | 3-(5-Bromo-3-nitro-pyridin-2-ylamino)-5-isopropyl-5-phenyl-dihydro-furan-2-one |
| 43 | 5-Isopropyl-3-(5-nitro-pyridin-2-ylamino)-5-phenyl-dihydro-furan-2-one |
| 44 | 5-Methyl-5-naphthalen-2-yl-3-(5-nitro-pyridin-2-ylamino)-dihydro-furan-2-one |
| 45 | 5-Isopropyl-5-phenyl-3-(pyrimidin-2-ylamino)-dihydro-furan-2-one |
| 46 | 3-[5-(4-Iodo-phenyl)-5-methyl-2-oxo-tetrahydro-furan-3-ylamino]-1H-pyrazole-4-carboxylic acid ethyl ester |
| 47 | 5-(4-Bromo-phenyl)-3-(5-bromo-pyridin-2-ylamino)-5-methyl-dihydro-furan-2-one |
| 48 | 3-(3-Bromo-5-methyl-pyridin-2-ylamino)-5-methyl-5-naphthalen-1-yl-dihydro-furan-2-one |
| 49 | 5-Methyl-5-naphthalen-1-yl-3-(6-propyl-pyridin-2-ylamino)-dihydro-furan-2-one |
| 50 | 5-(3-Chloro-phenyl)-5-methyl-3-(6-propyl-pyridin-2-ylamino)-dihydro-furan-2-one |
| 51 | 5-(3-Chloro-phenyl)-5-methyl-3-(4-methyl-3-nitro-pyridin-2-ylamino)-dihydro-furan-2-one |
| 52 | 5-(4-Bromo-phenyl)-5-methyl-3-(4-methyl-3-nitro-pyridin-2-ylamino)-dihydro-furan-2-one |
| 53 | 3-(5-Bromo-6-methyl-pyridin-2-ylamino)-5-methyl-5-naphthalen-1-yl-dihydro-furan-2-one |
| 54 | 3-(5-Bromo-6-methyl-pyridin-2-ylamino)-5-(4-iodo-phenyl)-5-methyl-dihydro-furan-2-one |
| 55 | 3-(3-Benzyloxy-pyridin-2-ylamino)-5-(4-iodo-phenyl)-5-methyl-dihydro-furan-2-one |
| 56 | 3-(3-Benzyloxy-pyridin-2-ylamino)-5-(4-bromo-phenyl)-5-methyl-dihydro-furan-2-one |
| 57 | 3-(4,6-Dimethyl-pyridin-2-ylamino)-5-(4-iodo-phenyl)-5-methyl-dihydro-furan-2-one |
| 58 | 5-(3-Chloro-phenyl)-3-(4,6-dimethyl-pyridin-2-ylamino)-5-methyl-dihydro-furan-2-one |
| 59 | 5-(4-Bromo-phenyl)-5-methyl-3-(3-methyl-pyridin-2-ylamino)-dihydro-furan-2-one |
| 60 | 5-(4-Bromo-phenyl)-5-methyl-3-(4-methyl-pyridin-2-ylamino)-dihydro-furan-2-one |
| 61 | 2-[5-(3,5-Dimethoxy-phenyl)-5-methyl-2-oxo-tetrahydro-furan-3-ylamino]-4-propyl-pyrimidine-5-carboxylic acid ethyl ester |

TABLE 2-continued

| Example | Name of compound: |
|---|---|
| 62 | 3-(4-Bromo-1H-pyrazol-3-ylamino)-5-(3,5-dimethoxy-phenyl)-5-methyl-dihydro-furan-2-one |
| 63 | 3-(4-Bromo-1H-pyrazol-3-ylamino)-5-(2-methoxy-phenyl)-5-methyl-dihydro-furan-2-one |
| 64 | 3-[5-(2,5-Dimethoxy-phenyl)-5-methyl-2-oxo-tetrahydro-furan-3-ylamino]-1H-pyrazole-4-carbonitrile |
| 65 | 3-[5-(2,5-Dimethoxy-phenyl)-5-methyl-2-oxo-tetrahydro-furan-3-ylamino]-5-methylsulfanyl-1H-pyrazole-4-carbonitrile |
| 66 | 5-(2,5-Dimethoxy-phenyl)-5-methyl-3-(pyridin-2-ylamino)-dihydro-furan-2-one |
| 67 | 5-(2-Methoxy-phenyl)-5-methyl-3-(pyridin-2-ylamino)-dihydro-furan-2-one |
| 68 | 3-(3-Chloro-5-trifluoromethyl-pyridin-2-ylamino)-5-(3,5-dimethoxy-phenyl)-5-methyl-dihydro-furan-2-one |
| 69 | 3-(3-Chloro-5-trifluoromethyl-pyridin-2-ylamino)-5-(2,5-dimethoxy-phenyl)-5-methyl-dihydro-furan-2-one |
| 70 | 3-(3,5-Dichloro-pyridin-2-ylamino)-5-(2-methoxy-phenyl)-5-methyl-dihydro-furan-2-one |
| 71 | 3-(3-Chloro-5-trifluoromethyl-pyridin-2-ylamino)-5-(2,4-dimethoxy-phenyl)-5-methyl-dihydro-furan-2-one |
| 72 | 3-(4,6-Dimethyl-pyridin-2-ylamino)-5-(3-methoxy-phenyl)-5-methyl-dihydro-furan-2-one |
| 73 | 3-(4,6-Dimethyl-pyridin-2-ylamino)-5-(4-methoxy-phenyl)-5-methyl-dihydro-furan-2-one |
| 74 | 5-(3,4-Dimethoxy-phenyl)-3-(4,6-dimethyl-pyridin-2-ylamino)-5-methyl-dihydro-furan-2-one |
| 75 | 5-(4-Methoxy-phenyl)-5-methyl-3-(4-methyl-pyridin-2-ylamino)-dihydro-furan-2-one |
| 76 | 5-(2,5-Dimethoxy-phenyl)-5-methyl-3-(pyrazin-2-ylamino)-dihydro-furan-2-one |
| 77 | 5-Methylsulfanyl-3-(2-oxo-5-phenyl-5-propyl-tetrahydro-furan-3-ylamino)-1H-pyrazole-4-carbonitrile |

Molecular Pharmacological Investigation:

The γ-lactone compounds produced according to Examples 1 to 75 were tested, as described above, using the HTS-NOS assay. The measured inhibition of the nitrogen monoxide synthase by the compounds according to the examples (10 $\mu$M) is stated in Table 3 below:

TABLE 3

| Example no. | NOS (% inhibition) |
|---|---|
| 1 | 40 |
| 2 | 45 |
| 3 | 42 |
| 4 | 45 |
| 5 | 58 |
| 6 | 40 |
| 7 | 45 |
| 8 | 41 |
| 9 | 51 |
| 10 | 61 |
| 11 | 81 |
| 12 | 59 |
| 13 | 44 |
| 14 | 48 |
| 15 | 45 |
| 16 | 47 |
| 17 | 43 |
| 18 | 40 |
| 19 | 40 |
| 20 | 54 |
| 21 | 91 |
| 22 | 44 |
| 23 | 79 |

TABLE 3-continued

| Example no. | NOS (% inhibition) |
|---|---|
| 24 | 84 |
| 25 | 45 |
| 26 | 43 |
| 27 | 43 |
| 28 | 68 |
| 29 | 40 |
| 30 | 41 |
| 31 | 44 |
| 32 | 41 |
| 33 | 45 |
| 34 | 40 |
| 35 | 42 |
| 36 | 65 |
| 37 | 50 |
| 38 | 55 |
| 39 | 44 |
| 40 | 53 |
| 41 | 53 |
| 42 | 41 |
| 43 | 45 |
| 44 | 47 |
| 45 | 58 |
| 46 | 44 |
| 47 | 54 |
| 48 | 45 |
| 49 | 53 |
| 50 | 61 |
| 51 | 50 |
| 52 | 43 |
| 53 | 40 |
| 54 | 70 |
| 55 | 44 |
| 56 | 59 |
| 57 | 72 |
| 58 | 73 |
| 59 | 45 |
| 60 | 59 |
| 61 | 40 |
| 62 | 40 |
| 63 | 51 |
| 64 | 42 |
| 65 | 42 |
| 66 | 52 |
| 67 | 45 |
| 68 | 60 |
| 69 | 58 |
| 70 | 51 |
| 71 | 54 |
| 72 | 40 |
| 73 | 56 |
| 74 | 51 |
| 75 | 48 |

All the investigated γ-lactone compounds according to the examples exhibit good inhibition of nitrogen monoxide synthase.

What is claimed is:

1. A method of treating a migraine comprising administering to a patient a pharmaceutically effective amount of a pharmaceutical composition comprising at least one substituted γ-lactone compound of the formula I,

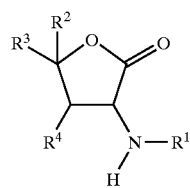

in which
$R^1$ denotes an optionally at least mono-substituted 2-pyridyl, 2-pyrimidyl, 3-pyrazolyl, 2-quinolinyl or 2-pyrazinyl residue, which may also be fused with a saturated or at least partially unsaturated hydrocarbon ring system, $R^2$ denotes an optionally at least mono-substituted, saturated, branched or unbranched aliphatic $C_{1-10}$ residue or an optionally at least mono-substituted, at least partially unsaturated, branched or unbranched aliphatic $C_{2-10}$ residue, $R^3$ denotes an optionally at least mono-substituted aryl residue, $R^4$ denotes H, or $R^3$ and $R^4$ together denote an optionally at least mono-substituted, saturated or at least mono-unsaturated aliphatic $C_{3-7}$ residue, with the proviso that the residue $R^2$ in this case denotes an optionally at least mono-substituted aryl residue, an optionally at least mono-substituted, saturated, branched or unbranched aliphatic $C_{1-10}$ residue or an optionally at least mono-substituted, at least partially unsaturated, branched or unbranched aliphatic $C_{2-10}$ residue, said compound being in the form of a racemate, a diastereomer or enantiomer as a free base or of a corresponding physiologically acceptable salt thereof.

2. A method according to claim 1, characterised in that $R^1$ denotes an optionally a least mono-substituted 2-pyridyl-residue, which may also be fused with a saturated or at least partially unsaturated hydrocarbon ring system, preferably denotes a 2-pyridyl residue which is substituted at least in position 4.

3. A method according to claim 1, characterised in that $R^2$ denotes an optionally a least mono-substituted, saturated, branched or unbranched aliphatic $C_{1-6}$-residue.

4. A method according to claim 1, characterised in that $R^3$ denotes an optionally a least mono-substituted aryl residue and $R^4$ denotes H.

5. A method according to claim 1, characterised in that the compound of formula I is selected from the group consisting of 5-(2,4-Dimethyl-phenyl)-3-(8-hydroxy-quinolin-2-ylamino)-5-methyl-dihydro-furan-2-one, 5-(3,4-Dimethyl-phenyl)-3-(4,6-dimethyl-pyridin-2-ylamino)-5-methyl-dihydro-furan-2-one, 5-(2,4-Dimethyl-phenyl)-3-(4,6-dimethyl-pyridin-2-ylamino)-5-methyl-dihydro-furan-2-one, 5-(4-Cyclohexyl-phenyl)-3-(4,6-dimethyl-pyridin-2-ylamino)-5-methyl-dihydro-furan-2-one, 5-(3,5-Dimethyl-phenyl)-3-(4,6-dimethyl-pyridin-2-ylamino)-5-methyl-dihydro-furan-2-one, 5-(3,4-Dimethyl-phenyl)-5-methyl-3-(4-methyl-pyridin-2-ylamino)-dihydro-furan-2-one, 5-(2,4-Dimethyl-phenyl)-5-methyl-3-(4-methyl-pyridin-2-ylamino)-dihydro-furan-2-one, 5-(4-Cyclohexyl-phenyl)-5-methyl-3-(4-methyl-pyridin-2-ylamino)-dihydro-furan-2-one, 5-Methyl-3-(quinolin-2-ylamino)-5-m-tolyl-dihydro-furan-2-one, 3-(4,6-Dimethyl-pyridin-2-ylamino)-5-methyl-5-p-tolyl-dihydro-furan-2-one, 3-(4,6-Dimethyl-pyridin-2-ylamino)-5-methyl-5-m-tolyl-dihydro-furan-2-one, 3-(4,6-Dimethyl-pyridin-2-ylamino)-5-(4-ethoxy-phenyl)-5-methyl-dihydro-furan-2-one, 4-[4-(3-Bromo-5-methyl-pyridin-2-ylamino)-2-methyl-5-oxo-tetrahydro-furan-2-yl]-benzonitrile, 3-(3-Bromo-5-methyl-pyridin-2-ylamino)-5-(4-tert-butyl-phenyl)-5-methyl-dihydro-furan-2-one, 5-(4-tert-Butyl-phenyl)-5-methyl-3-(6-propyl-pyridin-2-ylamino)-dihydro-furan-2-one, 5-(4-tert-Butyl-phenyl)-5-methyl-3-(4-methyl-3-nitro-pyridin-2-ylamino)-dihydro-furan-2-one, 3-(5-Bromo-6-methyl-pyridin-2-ylamino)-5-methyl-5-(4-phenoxy-phenyl)-dihydro-furan-2-one, 5-(4-tert-Butyl-phenyl)-5-methyl-3-(3-nitro-pyridin-2-ylamino)-dihydro-furan-2-one, 3-(3-Benzyloxy-pyridin-2-ylamino)-5-methyl-5-(4-phenoxy-phenyl)-dihydro-furan-2-one, 3-(3-Benzyloxy-pyridin-2-ylamino)-5-(4-tert-butyl-phenyl)-5-methyl-dihydro-furan-2-one, 3-(4,6-Dimethyl-pyridin-2-ylamino)-5-methyl-5-(4-phenoxy-phenyl)-dihydro-furan-2-one, 5-(4-tert-Butyl-phenyl)-3-(4,6-dimethyl-pyridin-2-ylamino)-5-methyl-dihydrofuran-2-one 5-Methyl-3-(4-methyl-pyridin-2-ylamino)-5-(4-phenoxy-phenyl)-dihydro-furan-2-one, 5-(4-tert-Butyl-phenyl)-5-methyl-3-(4-methyl-pyridin-2-ylamino)-dihydro-furan-2-one, 4-[4-(5-Bromo-3-nitro-pyridin-2-ylamino)-2-methyl-5-oxo-tetrahydro-furan-2-yl]-benzonitrile, 4-[4-(5-Bromo-pyrimidin-2-ylamino)-2-methyl-5-oxo-tetrahydro-furan-2-yl]-benzonitrile, 5-Benzo[b]thiophen-2-yl-5-methyl-3-(6-propyl-pyridin-2-ylamino)-dihydro-furan-2-one, 3-(4,6-Dimethyl-pyridin-2-ylamino)-5-(4-isopropyl-phenyl)-5-methyl-dihydro-furan-2-one, 5-Benzofuran-2-yl-3-(4,6-dimethyl-pyridin-2-ylamino)-5-methyl-dihydro-furan-2-one, 5-Benzo[b]thiophen-2-yl-5-methyl-3-(4-methyl-pyridin-2-ylamino)-dihydro-furan-2-one, 5-Benzofuran-2-yl-5-methyl-3-(4-methyl-pyridin-2-ylamino)-dihydro-furan-2-one, 3-(5-Benzo[1,3]dioxol-5-yl-5-methyl-2-oxo-tetrahydro-furan-3-ylamino)-1H-pyrazole-4-carbonitrile, 3-(5-Benzo[1,3]dioxol-5-yl-5-methyl-2-oxo-tetrahydro-furan-3-ylamino)-1H-pyrazole-4-carboxylic acid ethyl ester, 5-Benzo[1,3]dioxol-5-yl-5-methyl-3-(3-nitro-pyridin-2-ylamino)-dihydro-furan-2-one, 3-(4,6-Dimethyl-pyridin-2-ylamino)-5-methyl-5-(5,6,7,8-tetrahydro-naphthalen-2-yl)-dihydro-furan-2-one, 3-(4,6-Dimethyl-pyridin-2-ylamino)-5-methyl-5-naphthalen-2-yl-dihydro-furan-2-one, 5-Benzo[1,3]dioxol-5-yl-5-methyl-3-(4-methyl-pyridin-2-ylamino)-dihydro-furan-2-one, 5-Methyl-3-(4-methyl-pyridin-2-ylamino)-5-(5,6,7,8-tetrahydro-naphthalen-2-yl)-dihydro-furan-2-one, 5-Benzo[1,3]dioxol-5-yl-5-methyl-3-(5-methyl-pyridin-2-ylamino)-dihydro-furan-2-one, 5-Benzo[1,3]dioxol-5-yl-5-methyl-3-(6-methyl-pyridin-2-ylamino)-dihydro-furan-2-one, 3-(5-Bromo-3-nitro-pyridin-2-ylamino)-5-methyl-5-(5,6,7,8-tetrahydro-naphthalen-2-yl)-dihydro-furan-2-one, 3-(5-Bromo-3-nitro-pyridin-2-ylamino)-5-isopropyl-5-phenyl-dihydro-furan-2-one, 5-Isopropyl-3-(5-nitro-pyridin-2-ylamino)-5-phenyl-dihydro-furan-2-one, 5-Methyl-5-naphthalen-2-yl-3-(5-nitro-pyridin-2-ylamino)-dihydro-furan-2-one, 5-Isopropyl-5-phenyl-3-(pyrimidin-2-ylamino)-dihydro-furan-2-one, 3-[5-(4-Iodo-phenyl)-5-methyl-2-oxo-tetrahydro-furan-3-ylamino]-1H-pyrazole-4-carboxylic acid ethyl ester, 5-(4-Bromo-phenyl)-3-(5-bromo-pyridin-2-ylamino)-5-methyl-dihydro-furan-2-one, 3-(3-Bromo-5-methyl-pyridin-2-ylamino)-5-methyl-5-naphthalen-1-yl-dihydro-furan-2-one, 5-Methyl-5-naphthalen-1-yl-3-(6-propyl-pyridin-2-ylamino)-dihydro-furan-2-one, 5-(3-Chloro-phenyl)-5-methyl-3-(6-propyl-pyridin-2-ylamino)-dihydro-furan-2-one, 5-(3-Chloro-phenyl)-5-methyl-3-(4-methyl-3-nitro-pyridin-2-ylamino)-dihydro-furan-2-one, 5-(4-Bromo-phenyl)-5-methyl-3-(4-methyl-3-nitro-pyridin-2-ylamino)-dihydro-furan-2-one, 3-(5-Bromo-6-methyl-pyridin-2-ylamino)-5-methyl-5-naphthalen-1-yl-dihydro-furan-2-one, 3-(5-Bromo-6-methyl-pyridin-2-ylamino)-5-(4-iodo-phenyl)-5-methyl-dihydro-furan-2-one, 3-(3-Benzyloxy-pyridin-2-ylamino)-5-(4-iodo-phenyl)-5-methyl-dihydro-furan-2-one, 3-(3-Benzyloxy-pyridin-2-ylamino)-5-(4-bromo-phenyl)-5-methyl-dihydro-furan-2-one, 3-(4,6-Dimethyl-pyridin-2-ylamino)-5-(4-iodo-phenyl)-5-methyl-dihydro-furan-2-one, 5-(3-Chloro-phenyl)-3-(4,6-dimethyl-pyridin-2-ylamino)-5-methyl-dihydro-furan-2-one, 5-(4-Bromo-phenyl)-5-methyl-3-(3-methyl-pyridin-2-ylamino)-dihydro-furan-2-one, 5-(4-Bromo-phenyl)-5-methyl-3-(4-methyl-pyridin-2-ylamino)-dihydro-furan-2-one, 2-[5-(3,5-Dimethoxy-phenyl)-5-methyl-2-oxo-tetrahydro-furan-3-ylamino]-4-propyl-pyrimidine-5-carboxylic acid ethyl ester, 3-(4-Bromo-1H-pyrazol-3-ylamino)-5-(3,5-dimethoxy-phenyl)-5-methyl-dihydro-furan-2-one, 3-(4-Bromo-1H-pyrazol-3-ylamino)-5-(2-methoxy-phenyl)-5-methyl-dihydro-furan-2-one, 3-[5-(2,5-Dimethoxy-phenyl)-5-methyl-2-oxo-tetrahydro-furan-3-ylamino]-1H-pyrazole-4-carbonitrile, 3-[5-(2,5-Dimethoxy-phenyl)-5-methyl-2-oxo-tetrahydro-furan-3-ylamino]-5-methylsulfanyl-1H-pyrazole-4-carbonitrile, 5-(2,5-Dimethoxy-phenyl)-5-methyl-3-(pyridin-2-ylamino)-dihydro-furan-2-one, 5-(2-Methoxy-phenyl)-5-methyl-3-(pyridin-2-ylamino)-dihydro-furan-2-one, 3-(3-Chloro-5-trifluoromethyl-pyridin-2-ylamino)-5-(3,5-dimethoxy-phenyl)-5-methyl-dihydro-furan-2-one, 3-(3-Chloro-5-trifluoromethyl-pyridin-2-ylamino)-5-(2,5-dimethoxy-phenyl)-5-methyl-dihydro-furan-2-one, 3-(3,5-Dichloro-pyridin-2-ylamino)-5-(2-methoxy-phenyl)-5-methyl-dihydro-furan-2-one, 3-(3-Chloro-5-trifluoromethyl-pyridin-2-ylamino)-5-(2,4-dimethoxy-phenyl)-5-methyl-dihydro-furan-2-one, 3-(4,6-Dimethyl-pyridin-2-ylamino)-5-(3-methoxy-phenyl)-5-methyl-dihydro-furan-2-one, 3-(4,6-Dimethyl-pyridin-2-ylamino)-5-(4-methoxy-phenyl)-5-methyl-dihydro-furan-2-one, 5-(3,4-Dimethoxy-phenyl)-3-(4,6-dimethyl-pyridin-2-ylamino)-5-methyl-dihydro-furan-2-one, 5-(4-Methoxy-phenyl)-5-methyl-3-(4-methyl-pyridin-2-ylamino)-dihydro-furan-2-one, 5-(2,5-Dimethoxy-phenyl)-5-methyl-3-(pyrazin-2-ylamino)-dihydro-furan-2-one, 5-Methylsulfanyl-3-(2-oxo-5-phenyl-5-propyl-tetrahydro-furan-3-ylamino)-1H-pyrazole-4-carbonitrile and the corresponding physiologically acceptable salts thereof, preferably the hydrochlorides thereof.

6. A method of treating septic shock comprising administering to a patient a pharmaceutically effective amount of a pharmaceutical composition comprising at least one substituted γ-lactone compound of the formula I according to claim 1.

7. A method of treating a neurodegenerative disease comprising administering to a patient a pharmaceutically effective amount of a pharmaceutical composition comprising at least one substituted γ-lactone compound of the formula I according to claim 1.

8. A method according to claim 7, wherein the neurodegenerative disease is multiple sclerosis.

9. A method according to claim 7, wherein the neurodegenerative disease is Parkison's disease.

10. A method according to claim 7, wherein the neurodegenerative disease is Alzheimer's disease.

11. A method according to claim 7, wherein the neurodegenerative disease is Huntington's chorea.

12. A method of treating inflammation comprising administering to a patient a pharmaceutically effective amount of a pharmaceutical composition comprising at least one substituted γ-lactone compound of the formula I according to claim 1.

13. A method of treating inflammatory pain comprising administering to a patient a pharmaceutically effective amount of a pharmaceutical composition comprising at least one substituted γ-lactone compound of the formula I according to claim 1.

14. A method of treating cerebral ischaemia comprising administering to a patient a pharmaceutically effective amount of a pharmaceutical composition comprising at least one substituted γ-lactone compound of the formula I according to claim 1.

15. A method of treating diabetes comprising administering to a patient a pharmaceutically effective amount of a pharmaceutical composition comprising at least one substituted γ-lactone compound of the formula I according to claim 1.

16. A method of treating meningitis comprising administering to a patient pharmaceutically effective amount of a pharmaceutical composition comprising at least one substituted γ-lactone compound of the formula I according to claim 1.

17. A method of treating arteriosclerosis comprising administering to a patient a pharmaceutically effective amount of a pharmaceutical composition comprising at least one substituted γ-lactone compound of the general I according to claim 1.

18. A method of wound healing comprising administering to a patient a pharmaceutically effective amount of a pharmaceutical composition comprising at least one substituted γ-lactone compound of the formula I according to claim 1.

19. A method of treating neoplastic disease comprising administering to a patient a pharmaceutically effective amount of a pharmaceutical composition comprising at least one substituted γ-lactone compound of the formula I according to calim 1.

20. A method of treating a fungal disease comprising administering to a patient a pharmaceutically effective amount of a pharmaceutical composition comprising at least one substituted γ-lactone compound of the formula I according to claim 1.

* * * * *